US012697162B2

(12) United States Patent
Coates et al.

(10) Patent No.: US 12,697,162 B2
(45) Date of Patent: Aug. 4, 2026

(54) SYSTEMS AND METHODS FOR MEASURING PULSE WAVE VELOCITY

(71) Applicant: Medtronic Ireland Manufacturing Unlimited Company, Dublin (IE)

(72) Inventors: Paul J. Coates, Corte Madera, CA (US); Bijan Nafea, Santa Rosa, CA (US); Sahil Sharma, Santa Rosa, CA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 460 days.

(21) Appl. No.: 18/210,965

(22) Filed: Jun. 16, 2023

(65) Prior Publication Data

US 2024/0032982 A1      Feb. 1, 2024

Related U.S. Application Data

(60) Provisional application No. 63/393,682, filed on Jul. 29, 2022.

(51) Int. Cl.
  *A61B 18/12*        (2006.01)
  *A61B 18/14*        (2006.01)
  *A61B 18/00*        (2006.01)

(52) U.S. Cl.
  CPC ...... *A61B 18/1206* (2013.01); *A61B 18/1492* (2013.01); *A61B 2018/00577* (2013.01);
  (Continued)

(58) Field of Classification Search
  CPC ............ A61B 18/1206; A61B 18/1492; A61B 2018/00577; A61B 2018/00702;
  (Continued)

(56) References Cited

U.S. PATENT DOCUMENTS

| | | | |
|---|---|---|---|
| 5,423,323 A | 6/1995 | Orth | |
| 9,107,587 B2 | 8/2015 | Chemla et al. | |
| (Continued) | | | |

FOREIGN PATENT DOCUMENTS

| | | |
|---|---|---|
| CN | 114052896 A | 2/2022 |
| WO | 2014188430 A2 | 11/2014 |

OTHER PUBLICATIONS

Communication pursuant to Article 94(3) EPC issued in European Patent Application No. 23186421.1 dated Feb. 20, 2025.
(Continued)

*Primary Examiner* — Tigist S Demie
(74) *Attorney, Agent, or Firm* — Weber Roselli & Cannon LLP

(57)        ABSTRACT

A method for performing a therapeutic procedure includes applying therapy to target tissue, measuring a property of the target tissue at a plurality of spaced apart locations along the length of the target tissue, identifying changes in the measured property of the target tissue at each of the plurality of spaced apart locations, identifying a point in time at which the identified change in the measured property occurs at each of the plurality of spaced apart locations, and calculating a pulse wave velocity within the target tissue by comparing a difference between the identified points in time at which the identified change in the measured property occurs at at least two of the plurality of spaced apart locations, wherein the calculated pulse wave velocity is predictive of a response to therapy.

19 Claims, 10 Drawing Sheets

(52) U.S. Cl.
CPC .............. *A61B 2018/00702* (2013.01); *A61B 2018/00875* (2013.01)

(58) Field of Classification Search
CPC ........... A61B 2018/00797; A61B 2018/00875; A61B 2018/0212; A61B 2018/1861; A61B 5/02007; A61B 5/02125; A61B 5/02158; A61B 5/201; A61B 5/6852; G01S 17/42; G01S 17/931; G05B 19/406; G05B 2219/37572; G05B 2219/49137
See application file for complete search history.

(56) References Cited

U.S. PATENT DOCUMENTS

| | | | |
|---|---|---|---|
| 9,131,855 | B2 | 9/2015 | McEowen |
| 10,028,667 | B2 | 7/2018 | Kishida et al. |
| 10,893,809 | B2 | 1/2021 | Denney, Jr. et al. |
| 10,933,259 | B2 | 3/2021 | Sverdlik et al. |
| 10,959,622 | B2 | 3/2021 | Lading et al. |
| 2012/0065506 | A1 | 3/2012 | Smith |
| 2014/0276124 | A1 | 9/2014 | Cholette et al. |
| 2016/0113699 | A1* | 4/2016 | Sverdlik ................ A61N 7/022 606/27 |
| 2019/0223754 | A1 | 7/2019 | Gunasekaran et al. |
| 2020/0069196 | A1* | 3/2020 | Hettrick ............... A61B 5/0275 |

OTHER PUBLICATIONS

Aria et al., "Measuring Blood Pulse Wave Velocity with Bioimpedance in Different Age Groups", Sensors 2019, 19,850 (www.mdpi.com/journal/sensors).

Kouz et al., "Pulse Wave Analysis to Estimate Cardiac Output", Anesthesiology, V. 134 No. 1, Jan. 2021 ,pp. 119-126.

Extended European Search report issued in European Patent Application No. 23186428.1 dated Feb. 21, 2024.

Karl E.Engier et al: Pulse Wave Velocity Predicts Response to Renal Denervation in Isolated Systolic Hypertensionr, .Journal. of the American Heart Association,vol. 6, No. 5, May 5, 2017 (May 5, 2017), XP055547892.

* cited by examiner

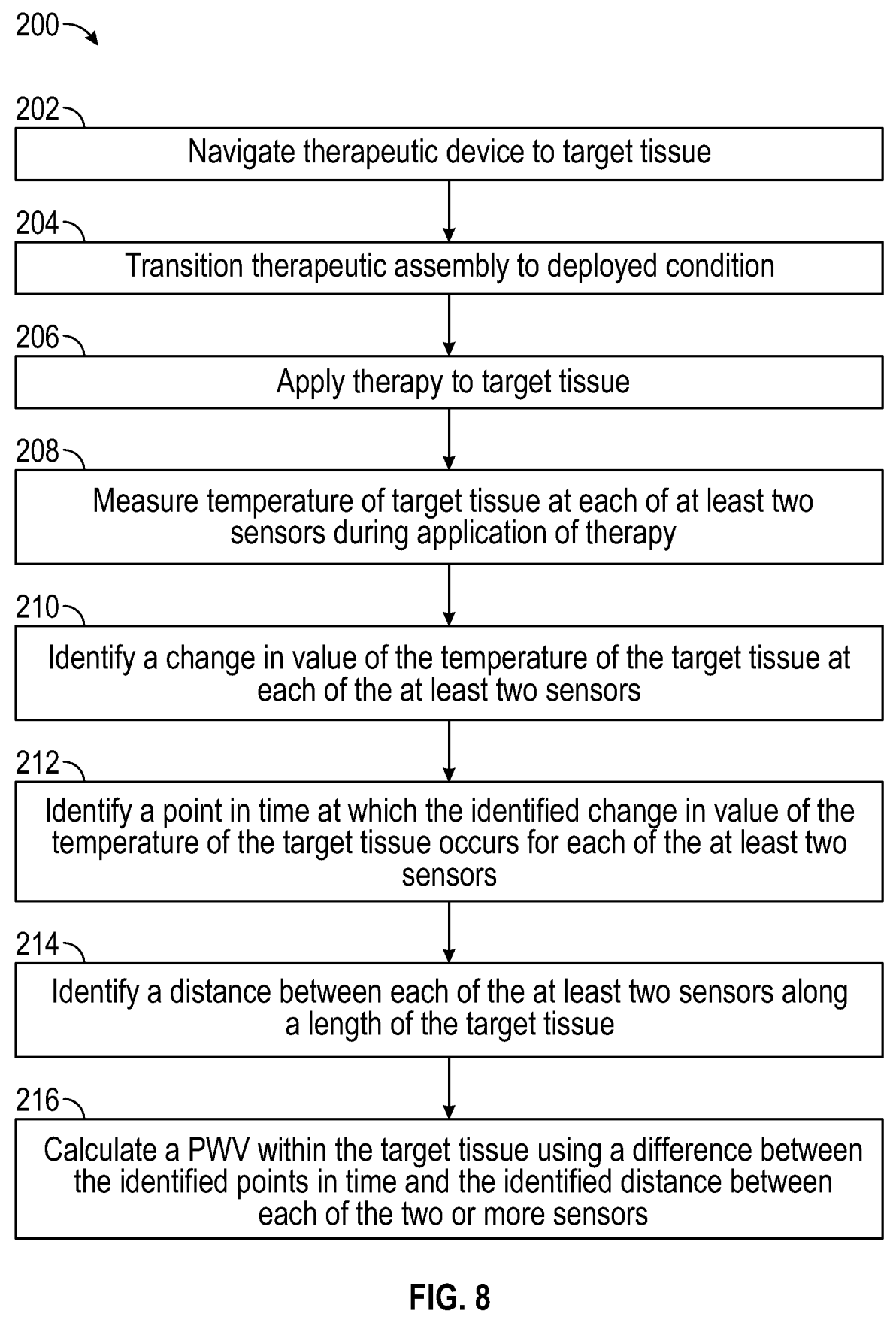

200

202
Navigate therapeutic device to target tissue

204
Transition therapeutic assembly to deployed condition

206
Apply therapy to target tissue

208
Measure temperature of target tissue at each of at least two sensors during application of therapy 210
Identify a change in value of the temperature of the target tissue at each of the at least two sensors 212
Identify a point in time at which the identified change in value of the temperature of the target tissue occurs for each of the at least two sensors 214
Identify a distance between each of the at least two sensors along a length of the target tissue 216
Calculate a PWV within the target tissue using a difference between the identified points in time and the identified distance between each of the two or more sensors

FIG. 8

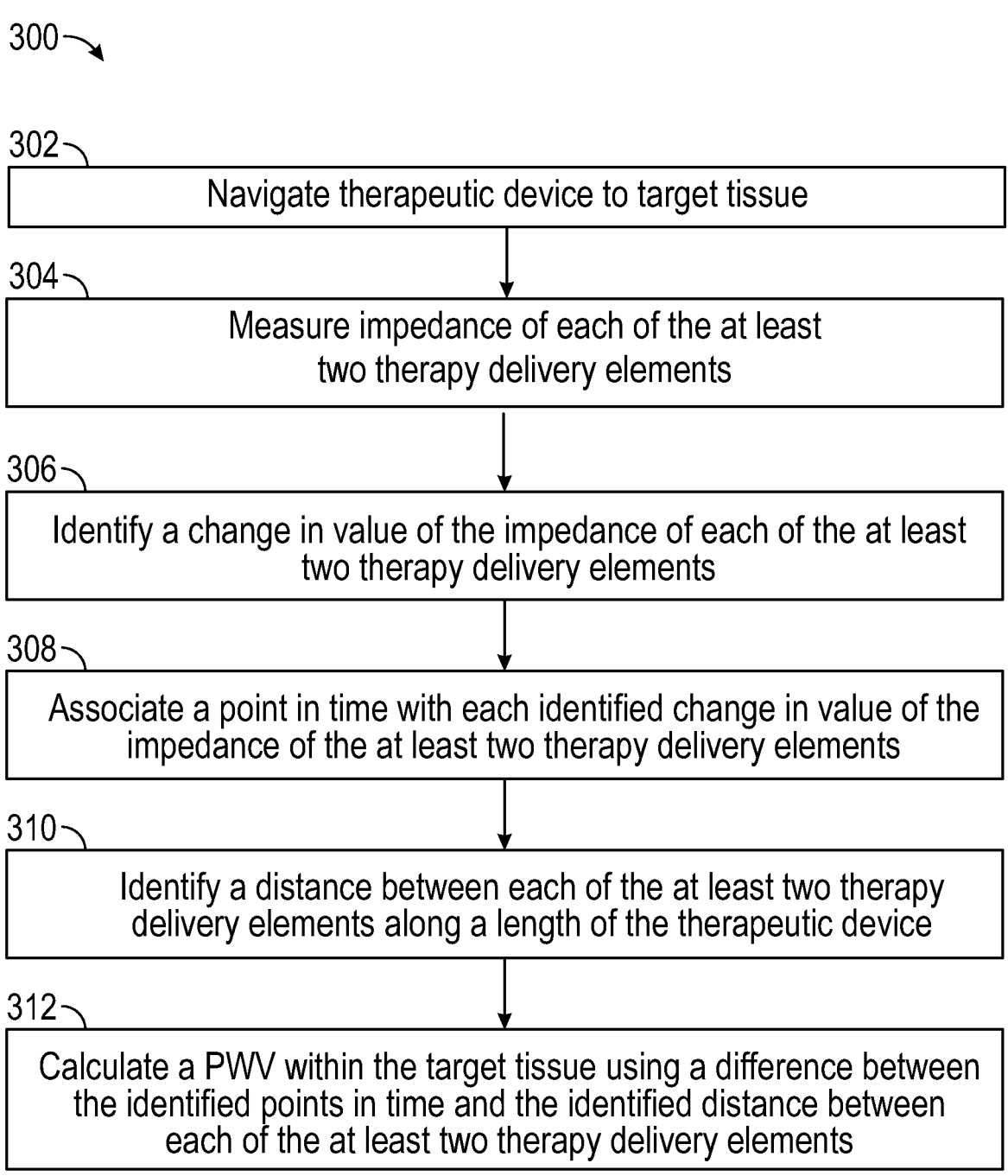

300

302
Navigate therapeutic device to target tissue

304
Measure impedance of each of the at least
two therapy delivery elements

306
Identify a change in value of the impedance of each of the at least
two therapy delivery elements 308
Associate a point in time with each identified change in value of the
impedance of the at least two therapy delivery elements 310
Identify a distance between each of the at least two therapy
delivery elements along a length of the therapeutic device 312
Calculate a PWV within the target tissue using a difference between
the identified points in time and the identified distance between
each of the at least two therapy delivery elements

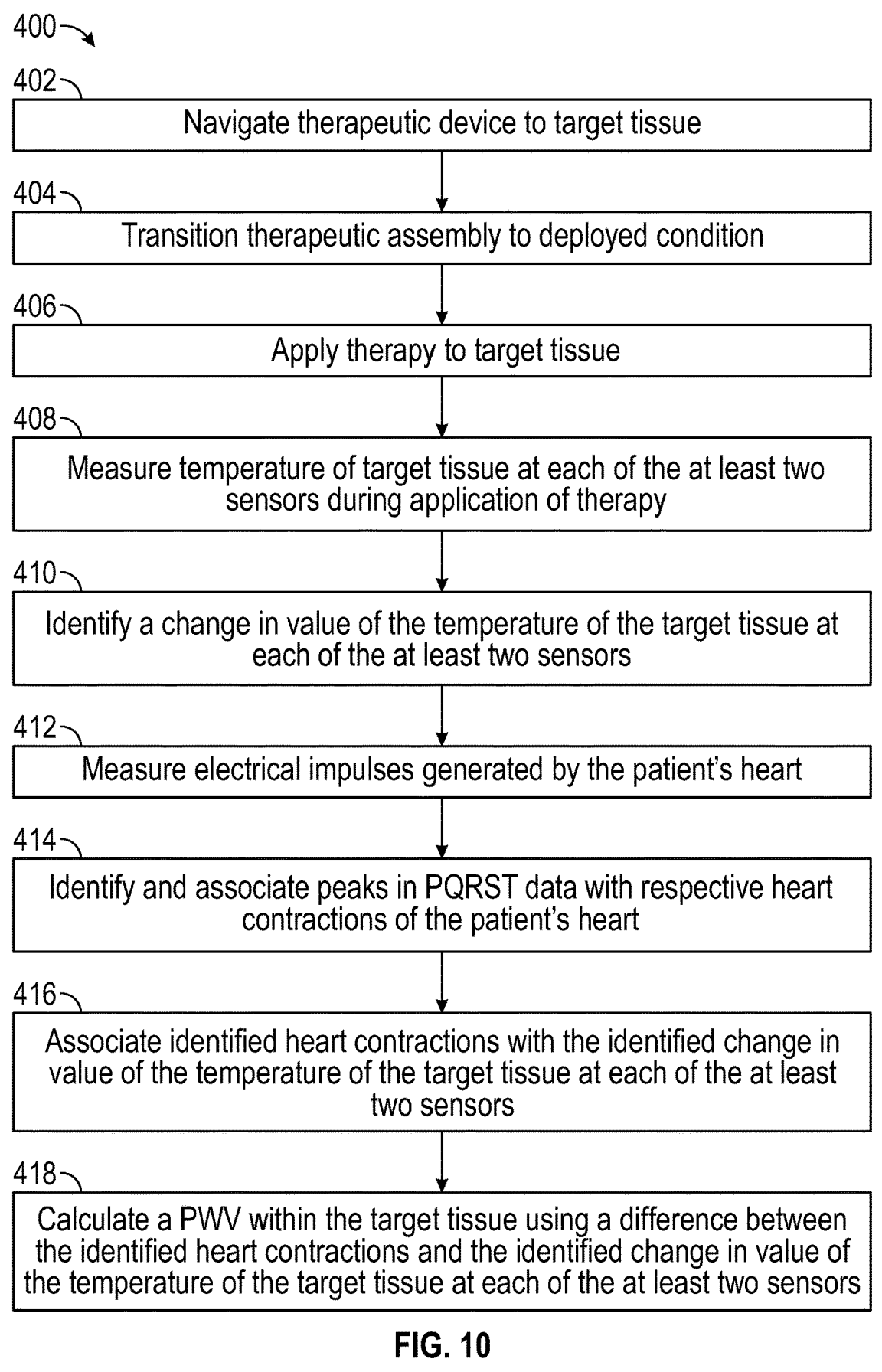

Navigate therapeutic device to target tissue

404

Transition therapeutic assembly to deployed condition

406

Apply therapy to target tissue

408

Measure temperature of target tissue at each of the at least two sensors during application of therapy

410

Identify a change in value of the temperature of the target tissue at each of the at least two sensors

412

Measure electrical impulses generated by the patient's heart

414

Identify and associate peaks in PQRST data with respective heart contractions of the patient's heart

416

Associate identified heart contractions with the identified change in value of the temperature of the target tissue at each of the at least two sensors

418

Calculate a PWV within the target tissue using a difference between the identified heart contractions and the identified change in value of the temperature of the target tissue at each of the at least two sensors

FIG. 10

SYSTEMS AND METHODS FOR MEASURING PULSE WAVE VELOCITY

CROSS-REFERENCE TO RELATED APPLICATION

This application claims the benefit of, and priority to, U.S. Provisional Patent Application Ser. No. 63/393,682, filed on Jul. 29, 2022, the entire content of which is hereby incorporated by reference herein.

TECHNICAL FIELD

The present disclosure relates to measuring pulse wave velocity and to predicting a response to or evaluating the procedural success of therapy.

BACKGROUND

Catheters have been proposed for use with various medical procedures. For example, a catheter can be configured to deliver neuromodulation (e.g., denervation) therapy to a target tissue site to modify the activity of nerves at or near the target tissue site. The nerves can be, for example, sympathetic nerves. The sympathetic nervous system (SNS) is a primarily involuntary bodily control system typically associated with stress responses. Chronic over-activation of the SNS is a maladaptive response that can drive the progression of many disease states. For example, excessive activation of the renal SNS has been identified experimentally and in humans as a likely contributor to the complex pathophysiology of arrhythmias, hypertension, states of volume overload (e.g., heart failure), and progressive renal disease.

Percutaneous renal denervation is a minimally invasive procedure that can be used to treat hypertension and other diseases caused by over-activation of the SNS. During a renal denervation procedure, a clinician delivers stimuli, therapy, or energy, such as radiofrequency, ultrasound, chemical, cooling, or other therapy to a treatment site to reduce activity of nerves surrounding a blood vessel. The stimuli, therapy, or energy delivered to the treatment site may provide various therapeutic effects through alteration of sympathetic nerve activity.

SUMMARY

In accordance with the present disclosure, a method of performing a therapeutic procedure includes predicting a response to and/or evaluating the procedural success of therapy, such as denervation therapy. In this manner, the method includes measuring a change in a property of target tissue over a period of time to calculate a Pulse Wave Velocity (PWV) within the target tissue. In certain aspects, the method includes applying therapy to target tissue, measuring a property of the target tissue at a plurality of spaced apart locations along the length of the target tissue during the application of therapy, identifying changes in the measured property of the target tissue at each of the plurality of spaced apart locations during the application of therapy, identifying a point in time at which the identified change in the measured property occurs at each of the plurality of spaced apart locations during the application of therapy, and calculating a pulse wave velocity within the target tissue by comparing a difference between the identified points in time at which the identified change in the measured property occurs at at least two of the plurality of spaced apart locations during the application of therapy, wherein the calculated pulse wave velocity is predictive of a response to therapy.

In aspects, measuring the property of the target tissue may include measuring a temperature of the target tissue at the plurality of spaced apart locations on the target tissue via a plurality of sensors associated with a therapeutic device during the application of therapy.

In other aspects, the method may include identifying a distance between each of the plurality of sensors.

In certain aspects, calculating the pulse wave velocity within the target tissue may include comparing the difference between the identified point in time at which the identified change in the measured temperature occurs at at least two of the plurality of sensors and the identified distance between the at least two of the plurality of sensors.

In other aspects, identifying changes in the measured property of the target tissue may include identifying one of a maximum of the change in the property, a minimum of the change in the property, an average of the change in the property, or a property of a derivative of the change in the property of the target tissue at each of the plurality of spaced apart locations during the application of therapy.

In aspects, identifying a point in time at which the identified change in measured property occurs may include identifying a point in time at which one of the maximum of the change in the property, the minimum of the change in the property, the average of the change in the property, or the property of the derivative of the change in the property of the target tissue is measured at each of the plurality of spaced apart locations during the application of therapy.

In certain aspects, calculating the pulse wave velocity within the target tissue may include comparing the identified points in time at which one of the maximum, minimum, average, or property of the derivative of the property is measured at a distal most location and a proximal most location of the plurality of spaced apart locations during the application of therapy.

In other aspects, identifying the distance between each of the plurality of sensors may include utilizing an imaging device to identify the distance between each of the plurality of sensors.

In aspects, the method may include advancing a therapeutic device including a plurality of sensors operably coupled thereto to the target tissue.

In certain aspects, measuring the change in the property of the target tissue may include measuring a change in impedance of the target tissue at the plurality of spaced apart locations on the target tissue during the application of therapy.

In accordance with another aspect of the present disclosure, a system for performing a therapeutic procedure includes a therapeutic device including a plurality of sensors disposed at a plurality of spaced apart locations along a length of a portion of the therapeutic device, and a computing device including a processor and a memory storing instructions, which when executed by the processor, cause the computing device to measure a change in a property of the target tissue at each of the sensors during an application of therapy from a portion of the therapeutic device to the target tissue, identify a point in time at which the measured change in the property of the target tissue occurs at each of the sensors during the application of therapy, and calculate a pulse wave velocity within the target tissue by comparing a difference between the identified point in time at which the measured change in the property of the target tissue occurs at at least two of the sensors during the application of therapy, wherein the calculated pulse wave velocity is predictive of a response to therapy.

In aspects, the instructions, when executed by the processor, may cause the processor to measure a change in temperature of the target tissue at each of the sensors during the application of therapy.

In other aspects, the instructions, when executed by the processor, may cause the processor to measure a change in impedance of the target tissue at each of the sensors during the application of therapy.

In certain aspects, the instructions, when executed by the processor, may cause the processor to identify a point in time at which one of a maximum of the change in property, a minimum of the change in property, an average of the change in property, or a property of a derivative of the change in property of the target tissue is measured at a distal most sensor and a proximal most sensor during the application of therapy.

In other aspects, the instructions, when executed by the processor, may cause the processor to calculate the pulse wave velocity within the target tissue by comparing the identified points in time at which one of the maximum, minimum, average, or property of the derivative of the change in property of the target tissue is measured at the distal most sensor and the proximal most sensor.

In aspects, the therapeutic device may include a plurality of therapy delivery elements disposed on a portion of the therapeutic device , the one or more therapy delivery elements configured to deliver therapy to the target tissue.

In accordance with another aspect of the present disclosure, a method of performing a therapeutic procedure includes applying therapy to target tissue via at least one therapy delivery element associated with a therapeutic device, measuring a change in a property of the target tissue at a plurality of spaced apart locations along the length of the target tissue via at least two sensors associated with the therapeutic device, and calculating a pulse wave velocity within the target tissue by comparing a difference between a point in time at which the identified change in the measured property occurs at each of the at least two sensors during the application of therapy, wherein the calculated pulse wave velocity is predictive of a response to therapy.

In aspects, measuring a change in the property of the target tissue via the at least two sensors may include measuring a change in temperature of the target tissue at the plurality of spaced apart locations along the length of the target tissue via at least two temperature sensors associated with the therapeutic device.

In other aspects, measuring the change in the property of the target tissue may include measuring the change in the property of the target tissue at the plurality of spaced apart locations along the length of the target tissue via the at least two sensors associated with the therapeutic device, the at least two sensors longitudinally offset from a location of the at least one therapy delivery element along the length of the target tissue.

In certain aspects, measuring the change in the property of the target tissue may include measuring the change in the property of the target tissue at the plurality of spaced apart locations along the length of the target tissue via at least two sensors associated with the therapeutic device, a first sensor of the at least two sensors disposed distal of the at least one therapy delivery element and a second sensor of the at least two sensors disposed proximal of the at least one therapy delivery element.

BRIEF DESCRIPTION OF THE DRAWINGS

Various aspects and embodiments of the disclosure are described hereinbelow with references to the drawings, wherein:

FIG. 8 is a flow chart illustrating a method of performing a therapeutic procedure provided in accordance with the present disclosure;

FIG. 9 is a flow chart illustrating another method of performing a therapeutic procedure provided in accordance with the present disclosure; and FIG. 10 is a flow chart illustrating yet another method of performing a therapeutic procedure provided in accordance with the present disclosure.

DETAILED DESCRIPTION

Figure 1:
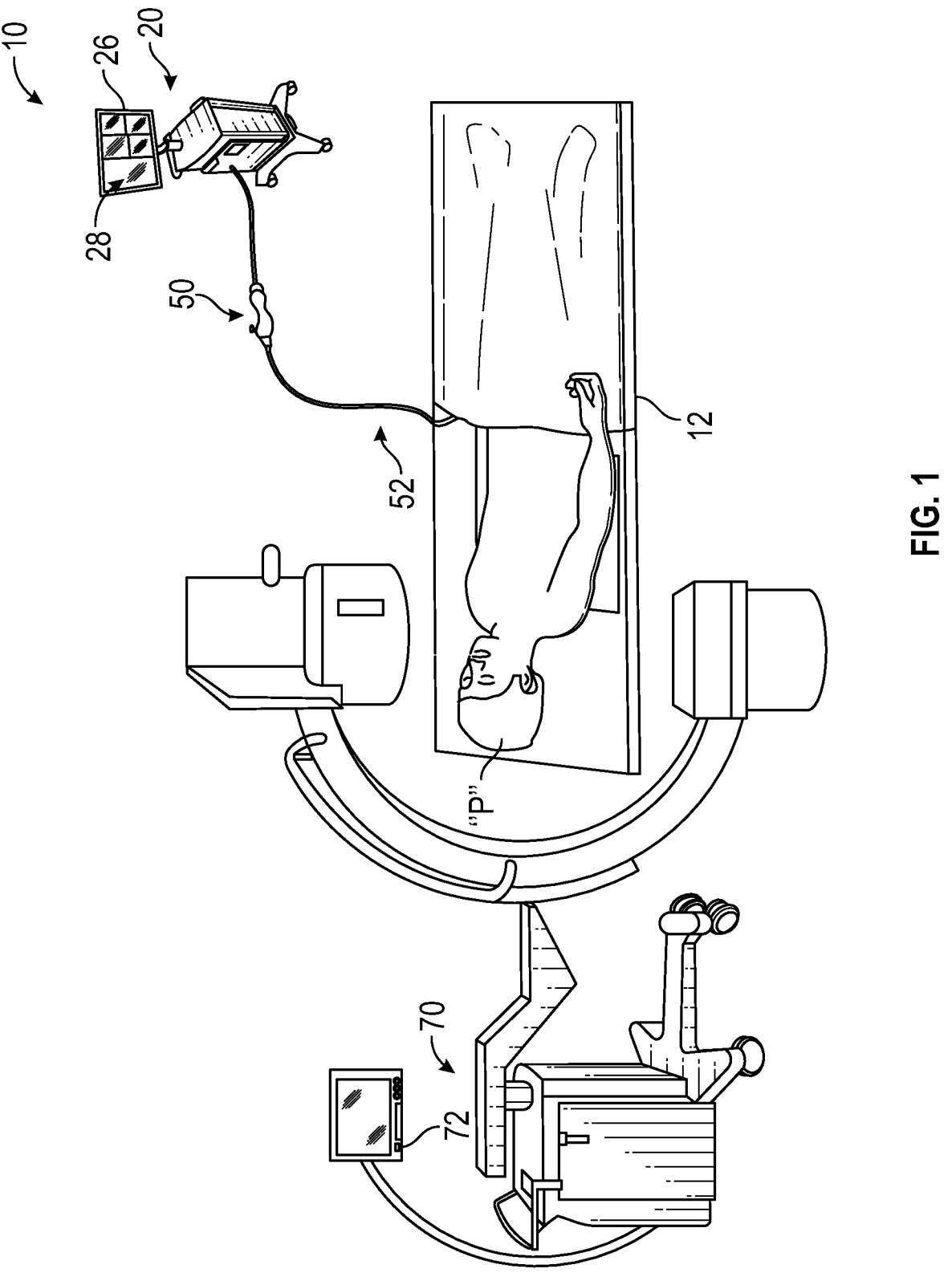
FIG. 1 is a schematic diagram of a therapeutic system provided in accordance with the present disclosure.

The present disclosure is directed to a therapeutic system that is configured to calculate a Pulse Wave Velocity (PWV) of fluid flowing within target tissue, and in embodiments, the flow of blood within the renal artery. The therapeutic system includes a therapy or energy source and a therapeutic device having a therapeutic assembly disposed on a distal end portion thereof. The therapeutic assembly of the therapeutic device includes one or more therapy delivery elements disposed thereon and in spaced relation to one another. In some embodiments, the therapeutic assembly may include four therapy delivery elements. The therapy delivery elements are in communication with the therapy source such that therapy delivered to the therapy delivery elements by the therapy source is applied or otherwise transmitted to the target tissue via each of the one or more therapy delivery elements. In embodiments, each of the therapy delivery elements includes a corresponding temperature sensor that is configured to measure a temperature of the target tissue in contact with the respective therapy delivery element. Although generally described as being associated with each of the therapy delivery elements, it is envisioned that the temperature sensors may be located at any suitable portion of the therapeutic assembly in contact with the target tissue that is affected by the therapy applied by the therapy delivery elements (within a therapy affected zone). The therapy source includes an algorithm that is configured to measure a temperature of the target tissue at each of the temperature sensors over a period of time during an application of therapy to the target tissue. Due to periodic pulses of blood over the target tissue due to each beat of the patient's heart, the target tissue in contact with each temperature sensor cools or otherwise decreases in temperature or heats or otherwise increases in temperature, depending upon the type of therapy being applied by the therapy delivery element. As the blood pulse travels as a wave, the change in temperature at each temperature sensor is delayed due to the distance between each of the temperature sensors along a length of the target tissue. The algorithm identifies a change in value of the temperature of the target tissue at each of the temperature sensors and associates the change in value of the temperature with point in time. A difference between the points in time the change in value of the temperature of the target tissue is calculated. A distance between each temperature sensor along a length of the target tissue is identified or calculated, and in embodiments, may be identified using an imaging device, such as fluoroscopic imaging. The PWV is calculated using the difference between the identified points in time and the identified distance between each of the temperature sensors.

In embodiments, the algorithm may measure an impedance value at each of the therapy delivery elements of the therapeutic assembly of the therapeutic device over a period of time. The algorithm identifies a change in value of the impedance as determined at each of the therapy delivery elements as each pulse of blood passes over the therapy delivery elements. The impedance of the target tissue and/or fluid contained within the target tissue changes due in part to changes in the diameter of the target tissue (e.g., renal artery). As can be appreciated, each pulse of blood flowing through the renal artery causes the renal artery to expand and contract due to increased pressure during each heartbeat. Therefore, the diameter, and therefore, the impedance, of the renal artery and/or the fluid within the renal artery is dynamic at all points in time, rather than just during the application of therapy. The algorithm utilizes the difference in time between the measured change in value of the impedance at each of the therapy delivery elements along with the distance between each of the therapy delivery elements to calculate the PWV of fluid flowing through the target tissue.

In embodiments, the therapeutic system may include an electrocardiogram (ECG) machine. The algorithm may identify peaks within the PQRST data obtained by the ECG machine, which may then be associated with heart contractions of the patient's heart. The algorithm may correlate the identified heart contractions with a change in temperature or a change in impedance measured at the temperature sensors or therapy delivery elements of the therapeutic device. The algorithm may identify a time difference between heart contraction measured by the ECG machine and the change in temperature and/or change in impedance of the target tissue to estimate a PWV of fluid flowing within the target tissue.

Although generally described as being applied to a patient's renal artery, it is envisioned that the systems and methods described herein may be applied to any suitable vasculature tissue within the patient's body. Those having skill in the art will recognize that although generally described as utilizing radiofrequency energy, it is envisioned that the therapeutic device may utilize microwave energy, ultrasound energy, electrical energy, cryogenic therapy, chemical therapy, etc., as will be described in further detail hereinbelow. While generally described as measuring a PWV of blood flowing within the target tissue as a predictor of a response to RDN therapy, it is contemplated that the PWV measurement may be performed before, during, and/or after the application of therapy to the target tissue to determine the efficacy of the treatment and whether the treatment should be repeated.

Turning now to the drawings, FIG. 1 illustrates a therapeutic system provided in accordance with the present disclosure and generally identified by reference numeral 10. As will be described in further detail hereinbelow, the therapeutic system 10 is generally configured to navigate a therapeutic device to a patient's renal artery, deliver therapy to a portion of the patient's renal artery, and identify a pulse wave velocity within the patient's renal artery.

The therapeutic system 10 includes a workstation 20, a therapeutic device 50 operably coupled to the workstation 20, and an imaging device 70, which in embodiments, may be operably coupled to the workstation 20. The patient "P" is shown lying on an operating table 12 with the therapeutic device 50 inserted through a portion of the patient's femoral artery, although it is contemplated that the therapeutic device 50 may be inserted into any suitable portion of the patient's vascular network that is in fluid communication with the patient's renal artery.

Figure 2:
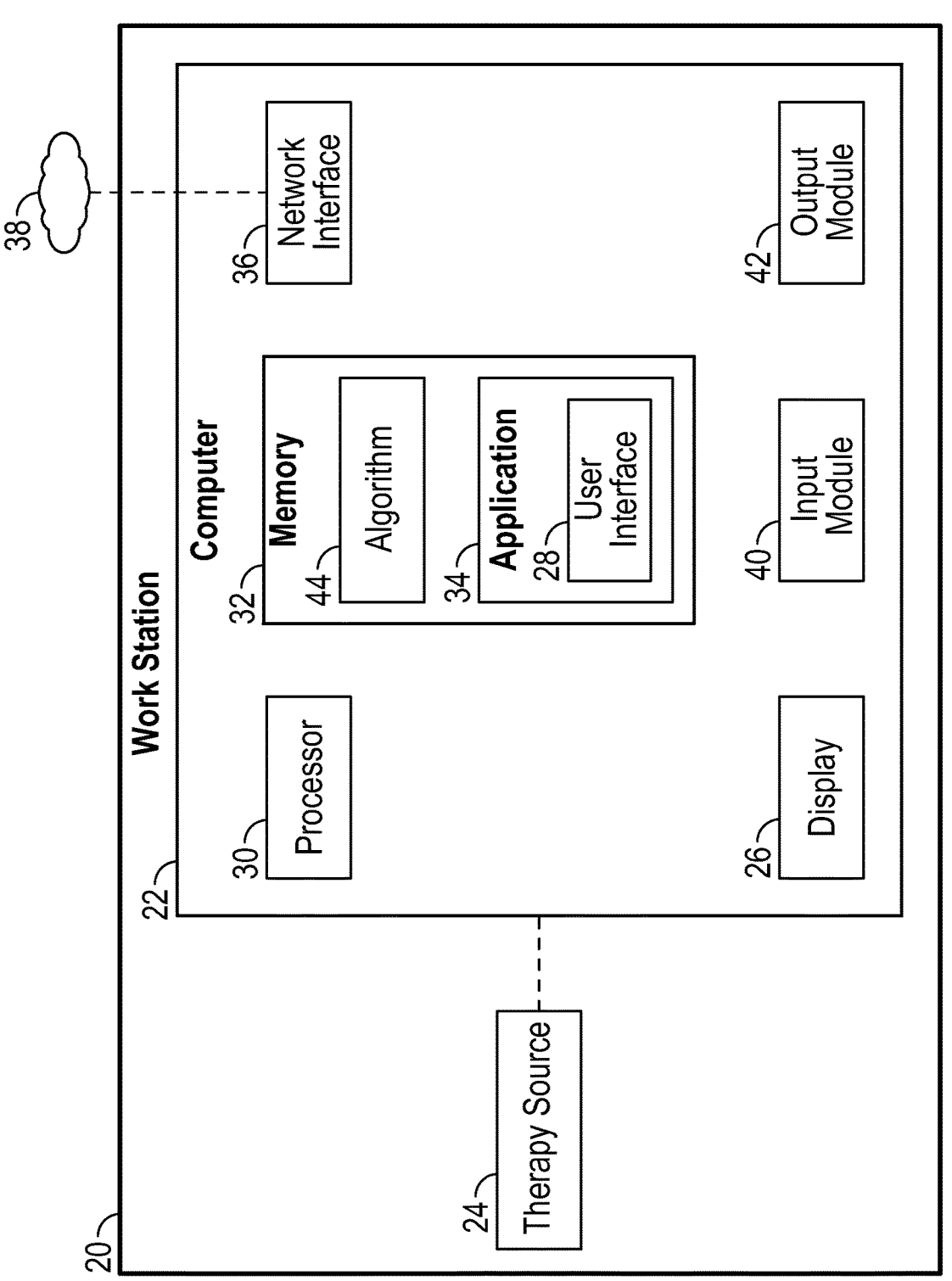
FIG. 2 is a schematic view of a workstation of the therapeutic system of FIG. 1.

Continuing with FIG. 1 and with additional reference to FIG. 2, the workstation 20 includes a computer 22 and a therapy source 24 (e.g., RF generator, microwave generator, ultrasound generator, heating and/or cooling source (electrical energy, cryotherapy, etc.), chemical source, etc.) operably coupled to the computer 22. The computer 22 is coupled to a display 26 that is configured to display one or more user interfaces 28. The computer 22 may be a desktop computer or a tower configuration with display 26 or may include a laptop computer or other computing device. The computer 22 includes a processor 30 which executes software stored in a memory 32. The memory 32 may store one or more applications 34 and/or algorithms 44 to be executed by the processor 30. A network interface 36 enables the workstation 20 to communicate with a variety of other devices and systems via the internet. The network interface 36 may connect the workstation 20 to the Internet via a wired or wireless connection. Additionally, or alternatively, the communication may be via an ad hoc Bluetooth® or wireless network enabling communication with a wide-area network (WAN) and/or a local area network (LAN). The network interface 36 may connect to the Internet via one or more gateways, routers, and network address translation (NAT) devices. The network interface 36 may communicate with a cloud storage system 38, in which further data, image data, and/or videos may be stored. The cloud storage system 38 may be remote from or on the premises of the hospital such as in a control or hospital information technology room. It is envisioned that the cloud storage system 38 could also serve as a host for more robust analysis of acquired images (e.g., fluoroscopic, CT, MRI, CBCT, etc.), data, etc. (e.g., additional or reinforcement data for analysis and/or comparison). An input module 40 receives inputs from an input device such as a keyboard, a mouse, voice commands, a therapy source controller (e.g., a foot pedal or handheld remote-control device that enables the clinician to initiate, terminate, and optionally, adjust various operational characteristics of the therapy source 24, including, but not limited to, power delivery), amongst others. An output module 42 connects the processor 30 and the memory 32 to a variety of output devices such as the display 26. In embodiments, the display 26 may be a touchscreen display.

The therapy source 24 generates and delivers therapy, such as radio frequency (RF) energy, microwave energy, ultrasound energy, heating or cooling therapy (e.g., electrical energy, cryotherapy, etc.) or in embodiments, may be a chemical source, via an automated control algorithm 44 stored on the memory 32 and/or under the control of a clinician. As can be appreciated, the energy and/or therapy generated and/or delivered by the therapy source 24 changes a temperature of the tissue (e.g., increases or decreases the temperature) along a length of the target tissue. In embodiments, the therapy source 24 may be configured to produce a selected modality and magnitude of energy and/or therapy for delivery to the treatment site via the therapeutic device 50, as will be described in further detail hereinbelow. In embodiments, the therapy source 24 monitors voltage and current applied to the target tissue via the therapeutic device 50, and in embodiments, monitors a temperature of the target tissue and/or a portion of the catheter, as will be described in further detail hereinbelow.

Figure 3:
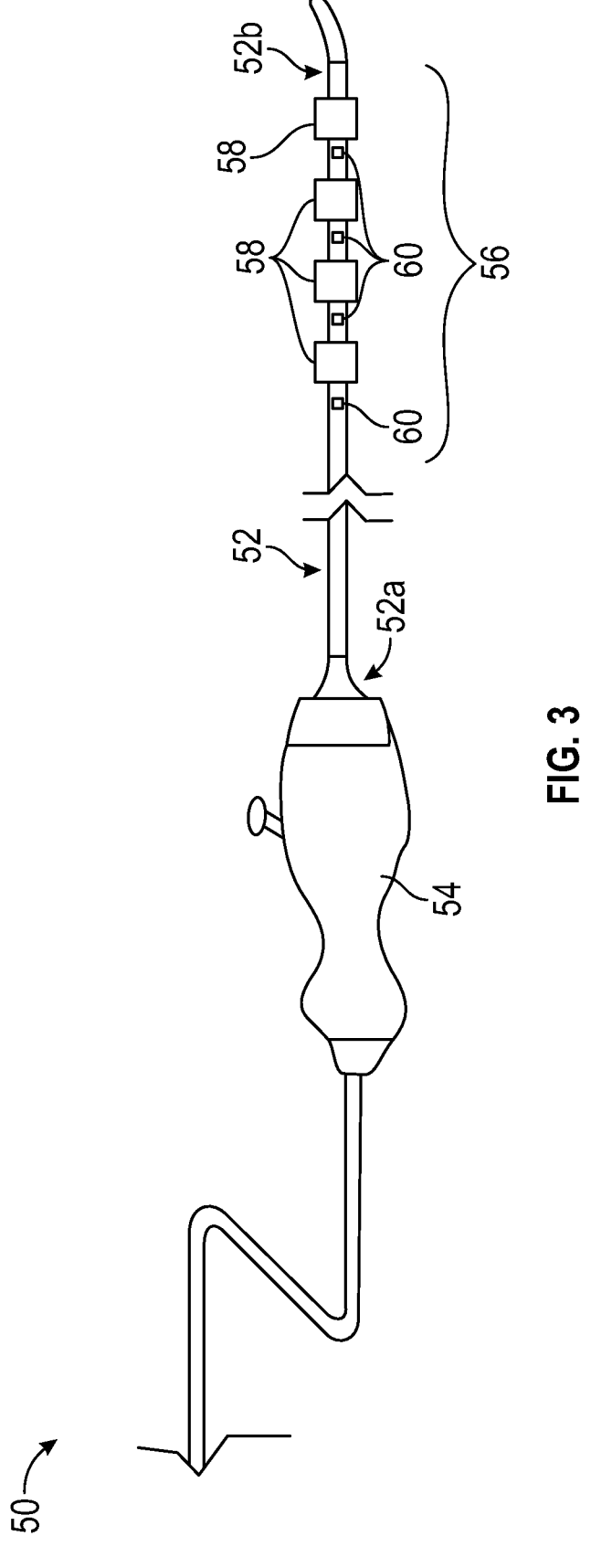
FIG. 3 is a perspective view of a therapeutic device of the therapeutic system of FIG. 1.
Figure 4:
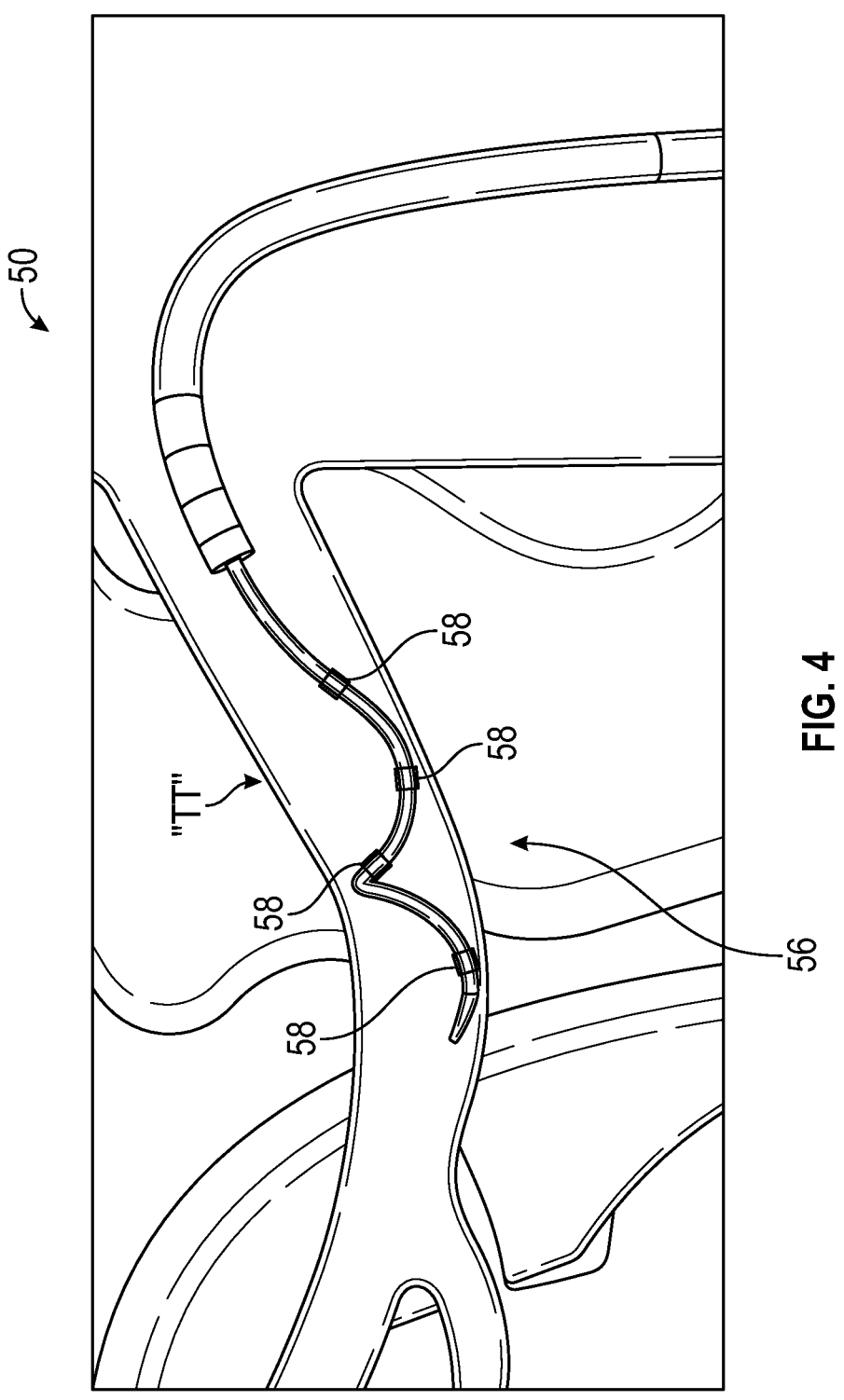
FIG. 4 is a perspective view of the therapeutic device of FIG. 3 shown advanced within a portion of the patient's anatomy and in a deployed condition.

With additional reference to FIGS. 3 and 4, the therapeutic device 50 includes an elongated shaft 52 having a handle 54 disposed on a proximal end portion 52*a* of the elongated shaft 52. The therapeutic device 50 includes a therapeutic assembly 56 disposed at a distal end portion 52*b* of the elongated shaft 52. The elongated shaft 52 of the therapeutic device 50 is configured to be advanced within a portion of the patient's vasculature, such as a femoral artery or other suitable portion of patient's vascular network that is in fluid communication with the patient's renal artery. In embodiments, the therapeutic assembly 56 is configured to be transformed from an initial, undeployed state having a generally linear profile (FIG. 3), to a second, deployed or expanded configuration, where the therapeutic assembly 56 forms a generally spiral and/or helical configuration (FIG. 4) for delivering therapy at the treatment site and providing therapeutically-effective electrically and/or thermally induced renal neuromodulation. In this manner, when in the second, expanded configuration, the therapeutic assembly 56 is pressed against or otherwise contacts the walls of the patient's vasculature tissue. Although generally described as transitioning to a spiral and/or helical configuration, it is envisioned that the therapeutic assembly 56 may be deployed to any suitable shape, and in embodiment, may include a linear shape. In embodiments, the therapeutic assembly may be capable of being placed in any suitable number of configurations, such as one, three, four, etc. depending upon the design needs of the therapeutic device or the type of therapeutic procedure being performed.

It is envisioned that the elongated shaft 52 may include an outer dimension that is configured to be received within a portion of a guide catheter or guide sheath (such as a 6F guide catheter) that is utilized to guide the elongated shaft 56, and therefore, the therapeutic assembly 56, to the ostium of the renal artery (for the guide catheter) or the target tissue (for the guide sheath), at which point if a guide sheath is utilized, the guide sheath is retracted a distance from the target area. In the case of the guide sheath, removal enables the therapeutic assembly 56 to transition from the first, undeployed state, to the second, deployed or expanded state. In embodiments utilizing the guide catheter or no guide catheter/guide sheath, the elongated shaft 52 may include an aperture (not shown) that is configured to slidably receive a guidewire (not shown) therethrough. In this manner, the guidewire is utilized to guide the elongated shaft 56, and therefore, the therapeutic assembly 56, to the target tissue using over-the-wire (OTW) or rapid exchange (RX) techniques, at which point the guide wire is removed from the target area, enabling the therapeutic assembly 56 to transition from the first, undeployed state, to the second, deployed or expanded state, although it is envisioned that the guide wire may remain at the target area, depending upon the therapeutic device being utilized and/or the procedure being performed. It is contemplated that the therapeutic assembly 56 may be transitioned from the first, undeployed state to the second, deployed state automatically (e.g., via a shape memory alloy, etc.) or manually (e.g., via pull wires, guide wire manipulation, etc. that is controlled by the clinician).

Continuing with FIGS. 3 and 4, in embodiments where the therapeutic device 50 is a RF ablation catheter, the therapeutic assembly 56 includes one or more therapy delivery elements or electrodes 58 disposed on an outer surface thereof that are configured to abut or otherwise contact a portion of the patient's vascular tissue when the therapeutic assembly 56 is placed in the second, expanded configuration. In an embodiment having two or more therapy delivery elements, the two or more therapy delivery elements 58 are disposed in spaced relation to one another along a length of the therapeutic assembly 56 and are in electrical communication with the therapy source 24 such that therapeutic energy (e.g., RF energy, microwave energy, etc.) generated by the therapy source 24 is transmitted or otherwise applied to the vascular tissue via the two or more therapy delivery elements 58. Although generally described as having two therapy delivery elements 58, it is envisioned that the therapeutic assembly 56 may include any suitable number of therapy delivery elements 58 disposed along a length thereof. It is envisioned that the therapy delivery elements 58 may deliver therapy independently of one another (e.g., monopolar), simultaneously, selectively, sequentially, and/or between any desired combination of the therapy delivery elements 28 (e.g., bipolar).

In one embodiment, the therapeutic device 50 may be a cryotherapy device where the therapeutic assembly 56 may include one therapy delivery element, such as an occlusive balloon, a non-occlusive balloon, or other balloon permitting the flow of blood, etc. In this embodiment, the therapy source 24 may include a cryogen or coolant source or means to generate a cryogen. It is envisioned that the therapeutic device 50 may be a microwave energy device where the therapeutic assembly 56 may include one or more therapy delivery elements, such as a microwave antenna. In this embodiment, the therapy source 24 may be a microwave energy generator that is operably coupled to the microwave antenna. It is contemplated that the therapeutic device 50 may be an ultrasound device where the therapeutic assembly 56 may include one or more therapy delivery elements, such as an ultrasound transducer, etc. In this embodiment, the therapy source 24 may be a radio-frequency energy generator or the like that is operably coupled to the ultrasound transducer. In embodiments, the therapeutic device 50 may be a chemical denervation device where the therapeutic assembly 56 may include one or more cannulas or needles for the administration of a chemical denervation agent. In this embodiment, the therapy source 24 may be a chemical denervation agent source that is operably coupled to the therapeutic assembly 56. Those having skill in the art will recognize that the therapeutic device 50, therapeutic assembly 56, and the therapy source 24 may be any suitable combination of devices capable of performing a denervation procedure.

Returning to FIGS. 3 and 4, in embodiments where the therapeutic device 50 is a RF ablation catheter, the therapeutic assembly 56 includes a temperature sensor 60 associated with each therapy delivery element 58 of the therapeutic assembly 56. In this manner, each of the two or more therapy delivery elements 58 includes a respective temperature sensor 60 coupled thereto such that the temperature sensors 60 measure a temperature of the respective therapy delivery elements 58 and/or the tissue in contact with the therapy delivery elements 58. It is envisioned that the temperature sensor 60 may be any suitable temperature sensing device, such as a thermocouple, a thermistor, etc. In embodiments, the two or more temperature sensors 60 may be disposed proximate to, on, or within a portion of a respective therapy delivery element 58.

Although generally described as being coupled to a respective therapy delivery element 58, it is envisioned that the temperature sensors 60 may be disposed at any portion along the length of the therapeutic assembly 56 that is in contact with a portion of the target tissue and may be a separate component from the one or more therapy delivery elements 58. In this manner, the two or more temperature sensors 60 measure a temperature of tissue that is impacted or otherwise influenced by the therapy delivered to the tissue by each respective therapy delivery element 58 (e.g., within the therapy and/or heat affected zone). In embodiments, the therapeutic assembly 56 may include a first temperature sensor 60 disposed distal of a distal most therapy delivery element 58 and a second temperature sensor 60 disposed proximal of a proximal most therapy delivery element 58 that is in contact with the target tissue (e.g., along a length of the target tissue that is affected by therapy delivery elements 58). Those having skill in the art will recognize that the therapeutic assembly 56 may include temperature sensors 60 associated with each therapy delivery element 58, temperature sensors 60 that are separate and distinct components from the therapy delivery elements 58 (e.g., measure a temperature of tissue within the therapy and/or heat affected zone of each therapy delivery element 58), or combinations thereof (e.g., a temperature sensor 60 associated with a therapy delivery element 58 and a temperature sensor 60 separate and distinct from the therapy delivery element 58 that measures a temperature of tissue within the therapy and/or heat affected zone of the therapy delivery element 58).

With reference to FIGS. 1 and 4-6, a pulse wave velocity (PWV) of blood flowing within the target artery can be calculated using a difference in time between a measured property of the target tissue and a distance between the points at which the measured change in property of the target tissue is identified (e.g., a transit time). In embodiments, the workstation 20 monitors a temperature of each of the one or more therapy delivery elements 58 and/or at each of the two or more temperature sensors 60 during application of therapy to the target tissue via the one or more therapy delivery elements 58. As can be appreciated, the two or more therapy delivery elements 58 and/or the two or more temperature sensors 60 are disposed in spaced relation to one another (e.g., a linear distance) along the length of the target tissue. Although the distance between each of the one or more therapy delivery elements 58 and/or the two or more temperature sensors 60 may be calculated or known during the manufacturing process, it is contemplated that the distance between each of the one or more therapy delivery elements 58 and/or the two or more temperature sensors 60 may be identified and/or confirmed using the imaging device 70 (e.g., fluoroscopic, CT, CBCT, Ultrasound, MRI, etc.) operably coupled to a display 72 and/or to the workstation 20. As described hereinabove, the two or more temperature sensors 60 measure a temperature of the one or more therapy delivery elements 58 or tissue disposed adjacent to but affected by (within the therapy and/or heat affected zone), the one or more therapy delivery elements 58.

As can be appreciated, during beating of the patient's heart (e.g., systole), pulses of blood pass over the target tissue, and therefore, each of the one or more therapy delivery elements 58 or temperature sensors 60. These pulses of blood passing over the target tissue cool or otherwise reduce a temperature of the target tissue in contact with the one or more therapy delivery elements 58 and/or temperature sensors 60. As can be appreciated, during a cryo-therapy procedure, the pulses of blood passing over the target tissue warms or otherwise increases a temperature of the target tissue in contact with the one or more therapy delivery elements 58 and/or two or more temperature sensors 60. During a resting period of the heart between pulses (e.g., diastole), the blood is not flowing as quickly as during the systole period, and therefore, does not cause as much cooling or heating of the tissue in contact with the one or more therapy delivery elements 58 and/or two or more temperature sensors 60. These oscillations in temperature are measured or otherwise identified by the two or more temperature sensors 60 over a period of time during the application of therapy to the target tissue.

In embodiments, the therapeutic assembly 56 of the therapeutic device 50 may include four therapy delivery elements 58 and a corresponding four temperature sensors 60, although it is envisioned that the therapeutic assembly 56 may include any suitable number of temperature sensors 60 and may be the same or different than the number of therapy delivery elements 58 (e.g., two, three, five, etc.). In one non-limiting embodiment, the therapeutic assembly 56 may include two temperature sensors 60; a first temperature sensor 60 disposed distal of the distal most therapy delivery element 58 and a second temperature sensor 60 disposed proximal of a proximal most therapy delivery element 58. In embodiments where the therapeutic assembly includes one therapy delivery element 58 (e.g., cryotherapy, chemical therapy, ultrasound, microwave, etc.), it is envisioned that the first temperature sensor 60 is disposed distal of the therapy delivery element 58 and the second temperature sensor 60 is disposed proximal of the therapy delivery element 58. During the application of therapy to the target tissue via the four therapy delivery elements 58, the temperature of the target tissue is different from body temperature (e.g., higher in the case of RF, microwave, ultrasound, chemical, etc. and lower in the case of cryotherapy). The flow of blood through the renal artery and therefore, over the four therapy delivery elements 58 occurs as a wave due to each pulse of the heart (e.g., the blood flows a distance of a certain period of time from a proximal most therapy delivery element 58 or temperature sensor towards a distal most therapy delivery element 58 or temperature sensor), which causes the target tissue to change in temperature. These oscillations in temperature (T1, T2, T3, and T4) are measured by each of the four temperature sensors 60 (FIG. 4) over a period of time during which the temperature is being modulated, such as, for example, between approximately 10 seconds and approximately 80 seconds, although it is contemplated that any suitable period of time may be utilized. As can be appreciated, feedback from the measurement of the PWV may require shortening or lengthening the period of time or modifying or modulating the delivery of therapy to the target tissue. As can be appreciated, the oscillations in temperature measured by the temperature sensors 60 correspond to systolic and diastolic conditions of the heart and are identified at different points in time since each of the four therapy delivery elements 58 and/or temperature sensors 60 are located at differing locations along the length of the target tissue.

Those having skill in the art will recognize that during chemical denervation therapy the temperature of the tissue may not change a sufficient amount to make an accurate measurement of the change in temperature. In this manner, in embodiments where the therapeutic device 50 is a chemical ablation catheter, the therapeutic assembly may include two or more impedance sensors (not shown) electrically coupled to the workstation 20 such that the workstation can measure the impedance at each of the two or more impedance sensors to determine a PWV within the tissue, as will be described in further detail hereinbelow.

Figure 5:
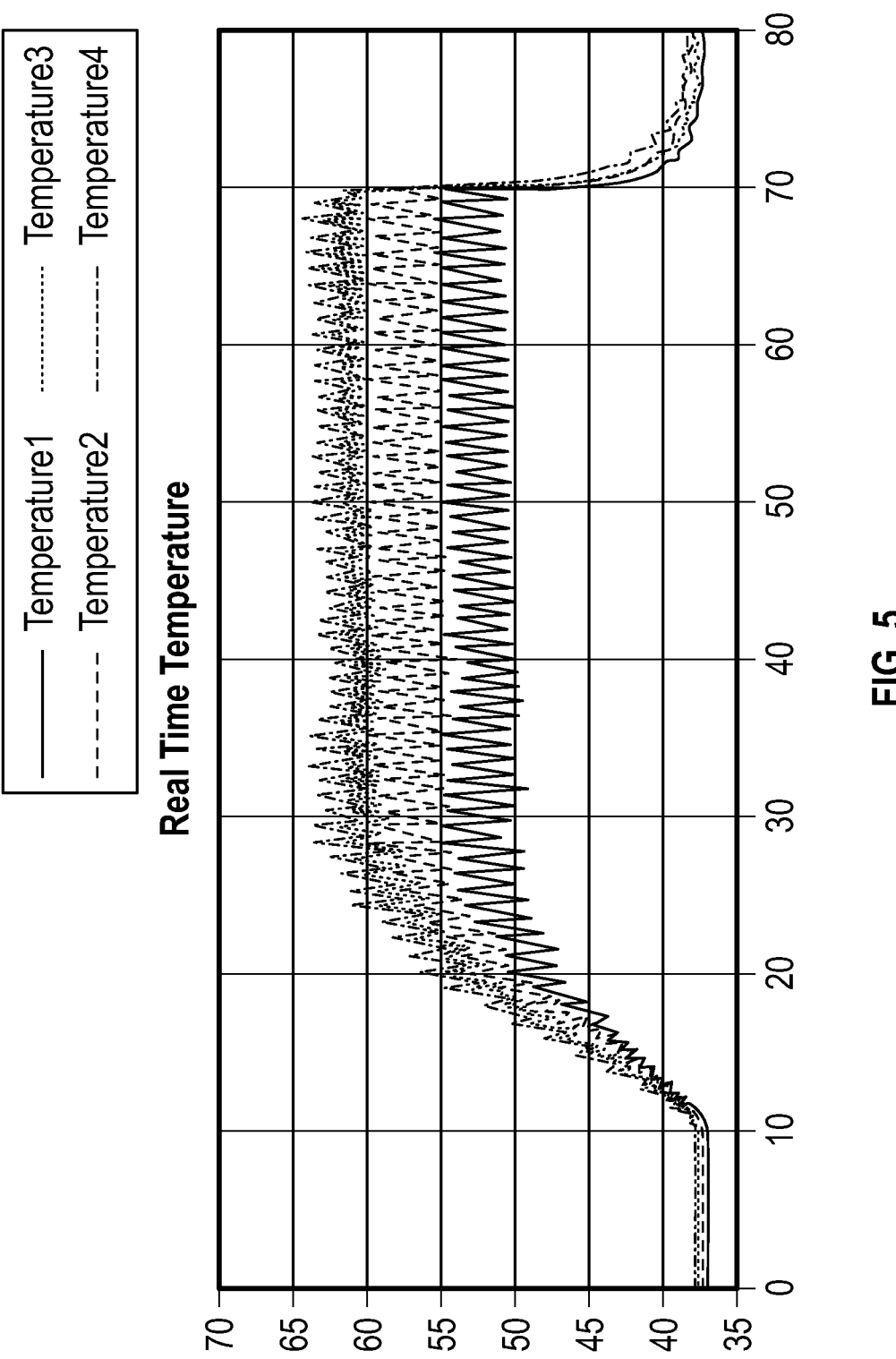
FIG. 5 is a schematic view of a change in a temperature of target tissue during the application of therapy to the target tissue.
Figure 6:
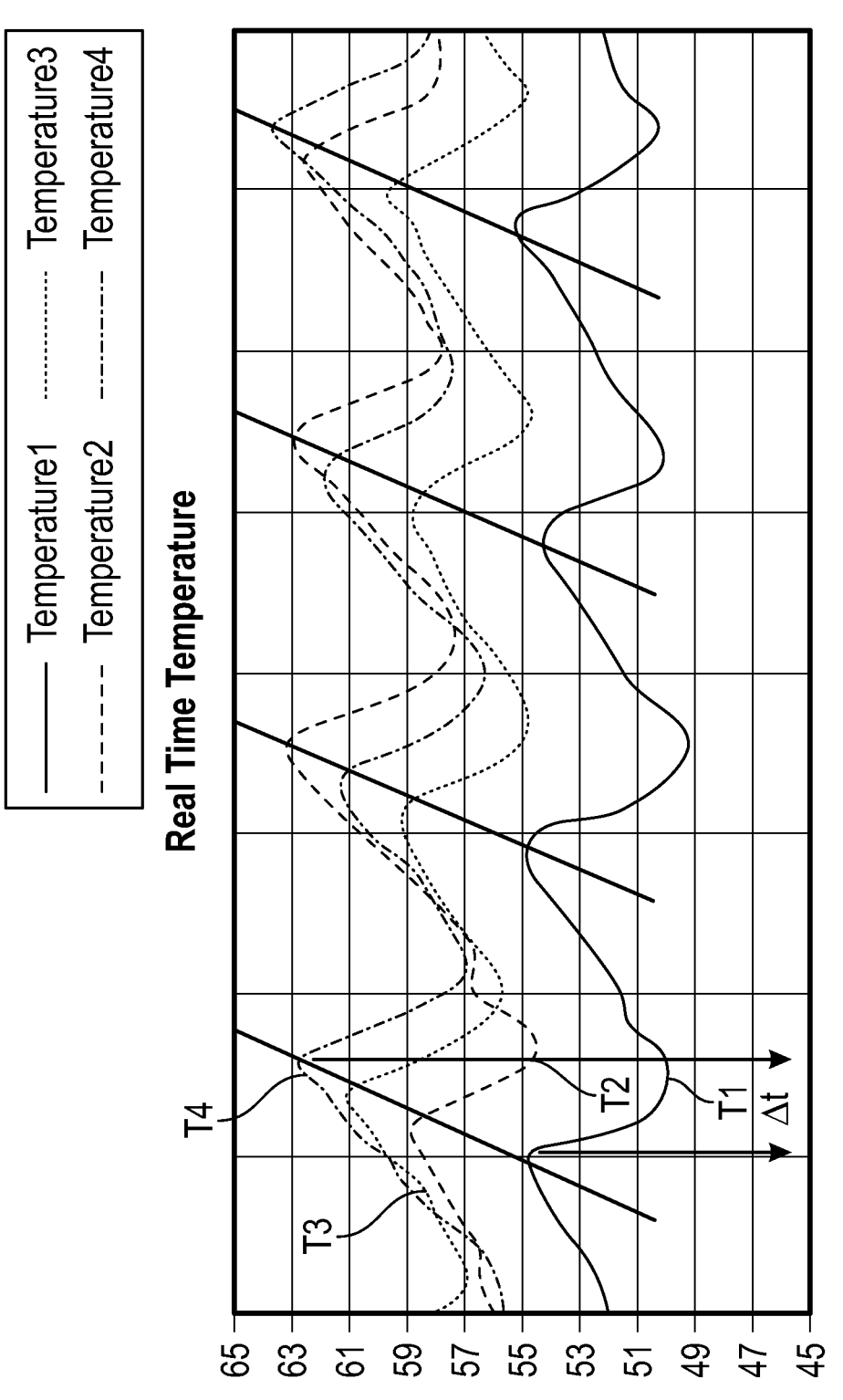
FIG. 6 is a schematic view of the change in the property of the target tissue of FIG. 4, illustrating a difference in time between a maximum value of the property of the target tissue at various locations along the target tissue

The workstation 20 identifies a maximum temperature measured by the four temperature sensors 60 associated with each of the four therapy delivery elements 58 (FIG. 5). As can be appreciated, the temperature of the tissue is periodic, and therefore, the maximum temperature refers to a local maxima or apex of the oscillatory profile of the temperature measurements over the period of time. Although generally described as identifying the maximum temperature, it is envisioned that the minimum temperature, an average in the change in temperature "ΔT," identification of consecutive inflection points (e.g., computing a second derivative and identifying a crossing point), amongst others may be utilized to identify a difference in time between a parameter measured by each of the four temperature sensors 60. Utilizing the identified difference in time between each maximum temperature measurement at each of the four therapy delivery elements 58 and the identified distance between each of the respective four therapy delivery elements 58, the PWV can be calculated. Although generally described as measuring the temperature at each of the four therapy delivery elements 58, it is envisioned that the temperature may be measured at any distinct therapy delivery element 58 and in embodiments, may be measured only at a proximal most therapy delivery element 58 and a distal most therapy delivery element 58 to provide a greater distance, and therefore, a greater amount of time, between each change in temperature, thereby increasing the accuracy of the PWV calculation.

As can be appreciated, the compliance (e.g., stiffness) of the target tissue affects the PWV within of the target artery. In this manner, less compliant arteries have a faster PWV, whereas more compliant arteries have a slower PWV. The PWV within the renal artery has been identified as a predictor of a response to Renal Denervation (RDN), in which patient's having a higher renal artery PWV are more likely to favorably respond to RDN treatment. In this manner, a higher PWV measured in the renal artery can be an indication of sympathetic-mediated arterial stiffness. As can be appreciated, the measurement of PWV may be performed before, during, and/or after the application of therapy to the target tissue. In this manner, the PWV may be monitored during the application of therapy to determine the efficacy of the treatment and the workstation 20 may adjust or modulate therapy delivery (e.g., more energy, less energy, terminate application of energy, more chemical agent, less chemical agent, terminate application of chemical agent, more cryogen, less cryogen, terminate flow of cryogen, etc.) based upon a change in the calculated PWV during the application of therapy. In this manner, the workstation 20 compares the calculated PWV to one or more predetermined thresholds as therapy is being applied to the target tissue. As can be appreciated, the one or more predetermined thresholds correspond to PWV calculations that are indicative of an insufficient amount of therapy being applied, a sufficient amount of therapy being applied, or an excess of therapy being applied to the target tissue, although one having skill in the art would envision any suitable number of predetermined thresholds that can be utilized. By continually or periodically monitoring the calculated PWV within the target tissue, the workstation 20 may continually or periodically increase, decrease, or maintain the intensity of therapy being applied to the target tissue. As can be appreciated, the one or more predetermined thresholds may be modified or otherwise tailored to correspond to the patient. In this manner, factors such as the patient's age, ethnicity, weight, medical history, amongst others can be utilized to develop a database of patient's having similar attributes for which the one or more predetermined thresholds can be assigned or the amount or intensity of therapy that must be applied to the target tissue.

In embodiments, the PWV may be calculated after therapy to determine the efficacy of the treatment and whether the treatment should be repeated, repeated with more energy, chemical agent, or cryogen, or applied at a different location. As described hereinabove with respect to monitoring PWV during the application of therapy, it is envisioned that the PWV calculated after the application of therapy may be compared to one or more predetermined thresholds. Using the one or more predetermined thresholds, the workstation 20 may determine if the application of therapy was insufficient or incomplete, sufficient, or an excess amount of therapy has been applied. It is envisioned that the workstation 20 may output one or more messages or alerts to the user regarding the efficacy of the application of therapy, such as a need to repeat the application of therapy and the intensity of therapy that must be applied and for how long, that the application of therapy was successful, etc. In embodiments, the workstation 20 may automatically resume the application of therapy if it is determined that the previous application of therapy was insufficient. The automatic resumption of the application of therapy can be applied at the same intensity, a greater intensity, or a lower intensity, depending upon the calculated PWV within the target tissue. As can be appreciated, any number of successive applications of therapy may be automatically resumed until the calculated PWV indicates that the application of therapy has been successful. It is envisioned that the workstation 20 may compare the number of successive application of therapy to a predetermined threshold, and if the number of applications of therapy exceeds the predetermined threshold, the workstation 20 may issue a message or alert to the user that the therapy does not appear to be effective and/or inhibit or otherwise prevent further application of therapy.

Figure 7:
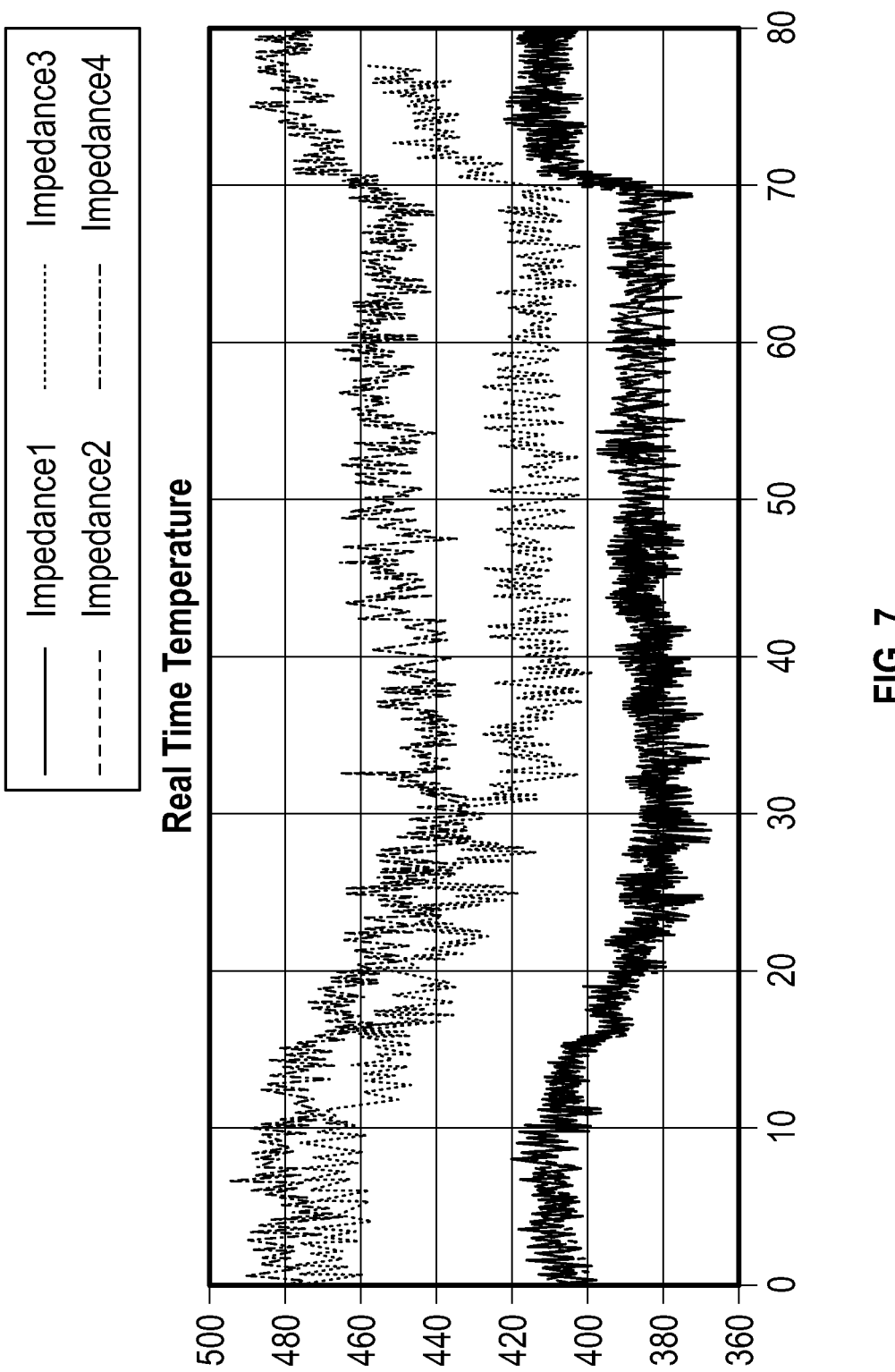
FIG. 7 is a schematic view of a change in impedance of sensors of the therapeutic device over a period of time.

With additional reference to FIG. 7, it is envisioned that the impedance at each of the four therapy delivery elements 58 can be measured by the workstation 20. In this manner, the workstation 20 monitors the current and voltage at each of the four therapy delivery elements 58 to identify an impedance of the load (e.g., tissue, fluid, etc.) applied to each of the four therapy delivery elements 58. In embodiments, during application of cryogenic energy, microwave energy, ultrasound energy, chemical energy, etc., additional sensors that may be a part of an electrical circuit (not shown) where a non-therapeutic voltage is applied (e.g., a voltage not capable of inducing therapy) may be disposed on a portion of the therapeutic assembly 56 such that during application of a cryogenic, the computer 22 monitors the current and voltage at the additional sensors (not shown) present in the target area that are not explicitly present to deliver therapy to the tissue. In contrast to a temperature change during the application of therapeutic energy via the four therapy delivery elements 58, an impedance of the target tissue changes due in part to changes in the diameter of the target tissue (e.g., renal artery). As can be appreciated, each pulse of blood flowing through the renal artery causes the renal artery to expand and contract due to increased pressure during each heartbeat. Therefore, the diameter, and therefore, the impedance, of the renal artery and/or the fluid within the renal artery is dynamic at all points in time, rather than just during the application of therapy. As a measurement of impedance at each of the four therapy delivery elements 58 can be taken regardless of whether the therapy delivery elements 58 are in contact with a tissue wall of the renal artery, it is envisioned that the impedance measurements at each of the therapy delivery elements 58 can be taken with the therapeutic assembly 56 placed in its initial, linear state. It is envisioned that the therapeutic assembly 56 may be generally centered within the renal artery. In embodiments, the therapy delivery elements 58 may be disposed on a separate element advanced within the renal artery separately from the therapeutic assembly 56. The distance between each of the four therapy delivery elements 58 is known, and therefore, it may be unnecessary to employ the use of the imaging device 70. Although generally described as measuring the impedance at each of the four therapy delivery elements 58, it is envisioned that the impedance may be measured only at a proximal most therapy delivery element 58 and a distal most therapy delivery element 58 to provide a greater distance, and therefore, a greater amount of time, between each change in impedance, thereby increasing the accuracy of the PWV calculation.

It is contemplated that the workstation 20 can identify a maximum value of impedance at each of the four therapy delivery elements 58 similarly to the identification of the maximum value of temperature at each of the four therapy delivery elements 58. The process of calculating a PWV within the target tissue using impedance is substantially similar to the calculation of PWV within the target tissue using temperature described hereinabove, and therefore, will not be described in detail herein in the interest of brevity.

In embodiments, the therapeutic system 10 may include an electrocardiogram machine (ECG machine) (not shown). It is envisioned that the workstation 20 may identify peaks within the PQRST data obtained by the ECG machine, which may then associate the identified peaks in the PQRST date with heart contractions of the patient's heart. The workstation 20 may correlate the identified heart contractions with a change in temperature or a change in impedance measured at the one or more therapy delivery elements 58 of the therapeutic device 50. The workstation 20 may identify a time difference between heart contraction measured by the ECG machine and the change in temperature of the target tissue to estimate a PWV within the target tissue. In embodiments, the workstation 20 may measure both temperature and impedance, both impedance and ECG data, or any combination thereof.

With reference to FIG. 8, a method of calculating a PWV within a target tissue is illustrated and generally identified by reference numeral 200. In step 202, the therapeutic assembly 56 of the therapeutic device 50 is navigated to the target tissue. Once the therapeutic assembly 56 of the therapeutic device 50 is located adjacent the target tissue, in step 204, the therapeutic assembly 56 is transitioned from the first, undeployed condition to the second, deployed condition such that the therapeutic assembly 56 forms a generally helical configuration and the one or more therapy delivery elements 58 abut a respective portion of the target tissue. In step 206, therapy is applied to the target tissue via the one or more therapy delivery elements 58. During the application of the therapy, in step 208, a temperature of the target tissue is measured by two or more temperature sensors 60 associated with a respective therapy delivery element of the one or more therapy delivery elements 58. In step 210, a change in the value of the temperature of the target tissue is identified adjacent each of the one or more therapy delivery elements 58. With the change in the measured temperature of the target tissue identified adjacent each of the one or more therapy delivery elements 58, a point in time at which the change in temperature is measured is identified for each of the one or more therapy delivery elements 58 in step 212. In step 214, a distance between each of the one or more temperature sensors 60 along a length of the target tissue is identified and in step 216, a PWV is calculated using a difference between the identified points in time and the identified distance between each of the two or more temperature sensors 60.

Turning to FIG. 9, another embodiment of a method of calculating a PWV within target tissue is illustrated and generally identified by reference numeral 300. In step 302, the therapeutic assembly 56 of the therapeutic device 50 is navigated to the target tissue. Once the therapeutic assembly 56 of the therapeutic device 50 is located adjacent the target tissue, in step 304, an impedance of each of the two or more therapy delivery elements 58 is measured over a period of time. In step 306, a change in the value of the impedance of the two or more therapy delivery elements 58 is identified and in step 308, a point in time is associated with each identified change in value of the impedance of the two or more therapy delivery elements 58. In step 310, a distance between each of the two or more therapy delivery elements 58 along the length of the therapeutic assembly 56 is identified and in step 312, a PWV is calculated using a difference between the identified points in time and the identified distance between each of the two or more therapy delivery elements 58.

With reference to FIG. 10, yet another embodiment of a method of calculating a PWV within target tissue is illustrated and generally identified by reference numeral 400. In step 402, the therapeutic assembly 56 of the therapeutic device 50 is navigated to the target tissue. Once the therapeutic assembly 56 of the therapeutic device 50 is located adjacent the target tissue, in step 404, the therapeutic assembly 56 is transitioned from the first, undeployed condition to the second, deployed condition such that the therapeutic assembly 56 forms a generally helical configuration and the two or more therapy delivery elements abut a respective portion of the target tissue. In step 406, therapy is applied to the target tissue via the two or more therapy delivery elements 58, and in step 408, a temperature of the target tissue is measured by the two or more temperature sensors 60 associated with a respective therapy delivery element of the two or more therapy delivery elements 58. In step 410, a change in the value of the temperature of the target tissue is identified adjacent each of the two or more therapy delivery elements 58. In step 412, electrical impulses generated by the patient's heart are measured by the ECG machine and in step 414, peaks in the PQRST data are identified and associated with respective heart contractions of the patient's heart. In step 416, the identified heart contractions are associated with the identified change in the value of the temperature of the target tissue and in step 418, a PWV within the target tissue is calculated using the difference in time between the identified heart contractions and the identified change in the value of the temperature of the target tissue.

Although described generally hereinabove, it is envisioned that the memory 32 may include any non-transitory computer-readable storage media for storing data and/or software including instructions that are executable by the processor 30 and which control the operation of the workstation 20 and, in some embodiments, may also control the operation of the therapeutic device 50, imaging device 70, and/or ECG machine. In an embodiment, memory 32 may include one or more storage devices such as solid-state storage devices, e.g., flash memory chips. Alternatively, or in addition to the one or more solid-state storage devices, the memory 32 may include one or more mass storage devices connected to the processor 30 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 30. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by the therapy source 24.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method of performing a therapeutic procedure, comprising:
    confirming in received images distances between a plurality of spaced apart locations along a length of target tissue;
    applying therapy to the target tissue;
    measuring a property of the target tissue at the plurality of spaced apart locations along the length of the target tissue during application of therapy;
    identifying changes in the measured property of the target tissue at each of the plurality of spaced apart locations during the application of therapy;
    identifying a point in time at which the identified change in the measured property occurs at each of the plurality of spaced apart locations during the application of therapy; and
    calculating a pulse wave velocity within the target tissue by comparing a difference between the identified points in time at which the identified change in the measured property occurs at at least two of the plurality of spaced apart locations during the application of therapy, wherein the calculated pulse wave velocity is predictive of a response to therapy.

2. The method according to claim 1, wherein measuring the property of the target tissue includes measuring a temperature of the target tissue at the plurality of spaced apart locations on the target tissue via a plurality of sensors associated with a therapeutic device during the application of therapy.

3. The method according to claim 1, wherein calculating the pulse wave velocity within the target tissue includes comparing the difference between the identified point in time at which the identified change in a measured temperature occurs at at least two of a plurality of sensors and a confirmed distance between the at least two of the plurality of sensors along the length of target tissue.

4. The method according to claim 3, wherein confirming in received images distances between a plurality of spaced apart locations along the length of target tissue comprises identifying a distance between each of the plurality of sensors.

5. The method according to claim 1, wherein identifying changes in the measured property of the target tissue includes identifying one of a maximum of the change in the property, a minimum of the change in the property, an average of the change in the property, or a property of a derivative of the change in the property of the target tissue is measured at each of the plurality of spaced apart locations during the application of therapy.

6. The method according to claim 5, wherein identifying a point in time at which the identified change in measured property occurs includes identifying a point in time at which one of the maximum of the change in the property, the minimum of the change in the property, the average of the change in the property, or the property of the derivative of the change in the property of the target tissue is measured at each of the plurality of spaced apart locations during the application of therapy.

7. The method according to claim 6, wherein calculating the pulse wave velocity within the target tissue includes comparing the identified points in time at which one of the maximum, minimum, average, or property of the derivative of the property is measured at a distal most location and a proximal most location of the plurality of spaced apart locations during the application of therapy.

8. The method according to claim 1, further comprising advancing a therapeutic device including a plurality of sensors operably coupled thereto to the target tissue.

9. The method according to claim 1, wherein measuring the change in the property of the target tissue includes measuring a change in impedance of the target tissue at the plurality of spaced apart locations on the target tissue during the application of therapy.

10. A system for performing a therapeutic procedure, comprising:
    a therapeutic device including a plurality of sensors disposed at a plurality of spaced apart locations along a length of a portion of the therapeutic device; and
    a computing device including a processor and a memory storing instructions, which, when executed by the processor, cause the computing device to:
        confirm in received images distances between each of the plurality of sensors;
        measure a change in a property of target tissue at each of the sensors during an application of therapy from a portion of the therapeutic device to the target tissue;
        identify a point in time at which the measured change in the property of the target tissue occurs at each of the sensors during the application of therapy; and
        calculate a pulse wave velocity within the target tissue by comparing a difference between the identified point in time at which the measured change in the property of the target tissue occurs at at least two of the sensors during the application of therapy, wherein the calculated pulse wave velocity is predictive of a response to therapy.

11. The system according to claim 10, wherein the instructions, when executed by the processor, cause the processor to measure a change in temperature of the target tissue at each of the sensors during the application of therapy.

12. The system according to claim 10, wherein the instructions, when executed by the processor, cause the processor to measure a change in impedance of the target tissue at each of the sensors during the application of therapy.

13. The system according to claim 10, wherein the instructions, when executed by the processor, cause the processor to identify a point in time at which one of a maximum of the change in the property, a minimum of the change in property, an average of the change in property, or a property of a derivative of the change in property of the target tissue is measured at a distal most sensor and a proximal most sensor during the application of therapy.

14. The system according to claim 13, wherein the instructions, when executed by the processor, cause the processor to calculate the pulse wave velocity within the target tissue by comparing the identified points in time at which one of the maximum, minimum, average, or property of the derivative of the change in the property of the target tissue is measured at the distal most sensor and the proximal most sensor.

15. The system according to claim 10, wherein the therapeutic device includes a plurality of therapy delivery elements disposed at a plurality of spaced apart locations along a length of a portion of the therapeutic device, the therapy delivery elements configured to deliver therapy to the target tissue.

16. A method of performing a therapeutic procedure, comprising:

confirming in received images a distance between each of at least two sensors associated with a therapeutic device along a length of target tissue;

applying therapy to the target tissue via at least one therapy delivery element associated with the therapeutic device;

measuring a change in a property of the target tissue at a plurality of spaced apart locations along the length of the target tissue via the at least two sensors associated with the therapeutic device; and calculating a pulse wave velocity within the target tissue by comparing a difference between a point in time at which the measured change in the property occurs at each of the at least two sensors during application of therapy, wherein the calculated pulse wave velocity is predictive of a response to therapy.

17. The method according to claim 16, wherein measuring a change in the property of the target tissue via the at least two sensors includes measuring a change in temperature of the target tissue at the plurality of spaced apart locations along the length of the target tissue via at least two temperature sensors associated with the therapeutic device.

18. The method according to claim 16, wherein measuring the change in the property of the target tissue includes measuring the change in the property of the target tissue at the plurality of spaced apart locations along the length of the target tissue via the at least two sensors associated with the therapeutic device, the at least two sensors longitudinally offset from a location of the at least one therapy delivery element along the length of the target tissue.

19. The method according to claim 18, wherein measuring the change in the property of the target tissue includes measuring the change in the property of the target tissue at the plurality of spaced apart locations along the length of the target tissue via at least two sensors associated with the therapeutic device, a first sensor of the at least two sensors disposed distal of the at least one therapy delivery element and a second sensor of the at least two sensors disposed proximal of the at least one therapy delivery element.

\* \* \* \* \*